(12) United States Patent
Wang et al.

(10) Patent No.: US 8,829,767 B2
(45) Date of Patent: Sep. 9, 2014

(54) LARGE-SCALE FABRICATION OF VERTICALLY ALIGNED ZNO NANOWIRE ARRAYS

(75) Inventors: Zhong Lin Wang, Marietta, GA (US); Youfan Hu, Atlanta, GA (US); Yan Zhang, Atlanta, GA (US); Chen Xu, Atlanta, GA (US); Guang Zhu, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 114 days.

(21) Appl. No.: 13/473,867

(22) Filed: May 17, 2012

(65) Prior Publication Data

US 2012/0293047 A1 Nov. 22, 2012

Related U.S. Application Data

(60) Provisional application No. 61/486,927, filed on May 17, 2011, provisional application No. 61/596,405, filed on Feb. 8, 2012.

(51) Int. Cl.
| | | |
|---|---|---|
| *H01L 41/113* | (2006.01) | |
| *H02N 2/18* | (2006.01) | |
| *B82Y 30/00* | (2011.01) | |
| *B82Y 5/00* | (2011.01) | |
| *H01L 27/20* | (2006.01) | |
| *B82Y 40/00* | (2011.01) | |
| *H01L 41/319* | (2013.01) | |

(52) U.S. Cl.
CPC *H02N 2/18* (2013.01); *B82Y 30/00* (2013.01); *B82Y 5/00* (2013.01); *H02N 2/181* (2013.01); *H01L 27/20* (2013.01); *B82Y 40/00* (2013.01); *H02N 2/186* (2013.01); *H01L 41/319* (2013.01); *H01L 41/113* (2013.01)
USPC .......................................................... 310/339

(58) Field of Classification Search
USPC ................................................... 310/329, 339
See application file for complete search history.

(56) References Cited

U.S. PATENT DOCUMENTS

| | | | | |
|---|---|---|---|---|
| 3,750,127 | A * | 7/1973 | Ayers et al. | 340/665 |
| 3,801,839 | A * | 4/1974 | Yo | 310/357 |
| 3,912,830 | A * | 10/1975 | Murayama et al. | 427/100 |
| 6,586,095 | B2 | 7/2003 | Wang et al. | |
| 7,220,310 | B2 | 5/2007 | Wang et al. | |
| 7,351,607 | B2 | 4/2008 | Wang et al. | |
| 7,705,523 | B2 | 4/2010 | Wang et al. | |

(Continued)

OTHER PUBLICATIONS

Jeon et al., "MEMS power generator with transverse mode thin film PCT," Science Direct, vol. 122, Issue 1, Jul. 29, 2005, pp. 16-22.

*Primary Examiner* — Derek Rosenau
(74) *Attorney, Agent, or Firm* — Bryan W. Bockhop; Bockhop & Associates, LLC

(57) ABSTRACT

A generator includes a substrate, a first electrode layer, a dense plurality of vertically-aligned piezoelectric elongated nanostructures, an insulating layer and a second electrode layer. The substrate has a top surface and the first electrode layer is disposed on the top surface of the substrate. The dense plurality of vertically-aligned piezoelectric elongated nanostructures extends from the first electrode layer. Each of the nanostructures has a top end. The insulating layer is disposed on the top ends of the nanostructures. The second electrode layer is disposed on the non-conductive layer and is spaced apart from the nanostructures.

23 Claims, 3 Drawing Sheets

(56) References Cited

U.S. PATENT DOCUMENTS

| | | |
|---|---|---|
| 7,898,156 B2 | 3/2011 | Wang et al. |
| 7,982,370 B2 * | 7/2011 | Wang et al. .......... 310/339 |
| 8,354,776 B2 * | 1/2013 | Choi et al. .......... 310/339 |
| 2003/0205657 A1 | 11/2003 | Voisin |
| 2004/0127025 A1 | 7/2004 | Crocker, Jr. et al. |
| 2005/0188751 A1 | 9/2005 | Puskas |
| 2005/0242366 A1 | 11/2005 | Parikh et al. |
| 2008/0067618 A1 | 3/2008 | Wang et al. |
| 2009/0066195 A1 | 3/2009 | Wang et al. |
| 2009/0115293 A1 | 5/2009 | Wang et al. |
| 2009/0179523 A1 | 7/2009 | Wang et al. |
| 2009/0209303 A1 | 8/2009 | Kroll et al. |
| 2010/0026142 A1 | 2/2010 | Jones et al. |
| 2010/0117488 A1 | 5/2010 | Wang et al. |
| 2010/0139750 A1 | 6/2010 | Kim et al. |
| 2010/0141095 A1 | 6/2010 | Park |
| 2010/0147371 A1 | 6/2010 | Cho |
| 2010/0171095 A1 | 7/2010 | Wang et al. |
| 2010/0191153 A1 | 7/2010 | Sanders et al. |
| 2010/0253184 A1 | 10/2010 | Choi et al. |
| 2010/0258160 A1 | 10/2010 | Wang et al. |
| 2010/0314968 A1 | 12/2010 | Mohamadi |
| 2011/0050042 A1 | 3/2011 | Choi et al. |
| 2011/0074564 A1 * | 3/2011 | Hirabayashi et al. ......... 340/447 |
| 2011/0107569 A1 | 5/2011 | Wang et al. |

\* cited by examiner

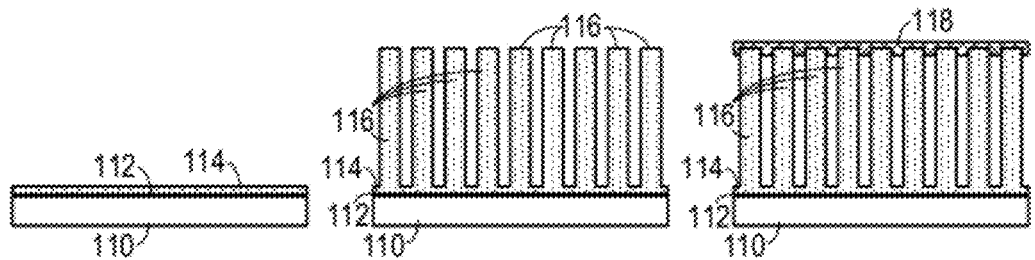
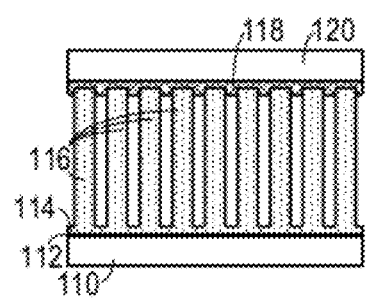 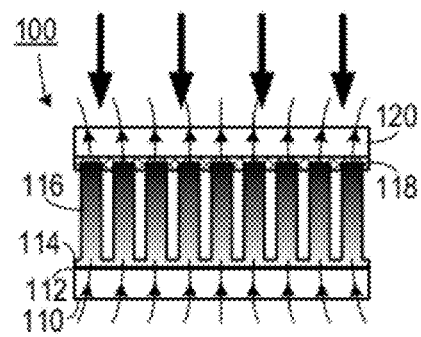
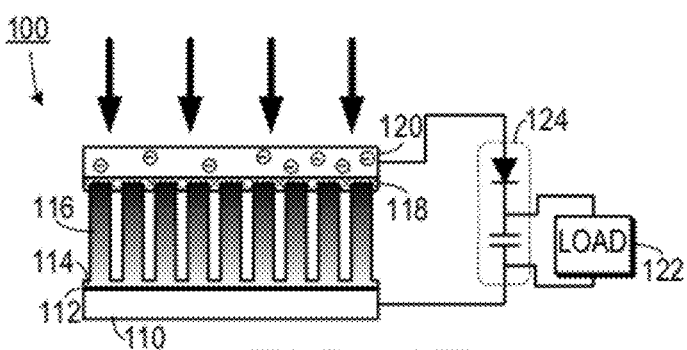

LARGE-SCALE FABRICATION OF VERTICALLY ALIGNED ZNO NANOWIRE ARRAYS

CROSS-REFERENCE TO RELATED APPLICATION(S)

This application claims the benefit of U.S. Provisional Patent Application Ser. No. 61/486,927, filed May 17, 2011, the entirety of which is hereby incorporated herein by reference. This application also claims the benefit of U.S. Provisional Patent Application Ser. No. 61/596,405, filed Feb. 8, 2012, the entirety of which is hereby incorporated herein by reference.

STATEMENT OF GOVERNMENT INTEREST

This invention was made with government support under contract No. DE-FG02-07ER46394, awarded by the Department of Energy. The government has certain rights in the invention.

BACKGROUND OF THE INVENTION

1. Field of the Invention

The present invention relates to power generators and, more specifically, to a power generator for harvesting ambient energy.

2. Description of the Related Art

Nanoscale and microscale devices are being in such diverse applications as sensors, transducers, data processors, control systems, communications systems and many more. Virtually all of these applications require a power source. While most nanoscale and microscale devices do not consume very much power, the wiring difficulties associated with such systems can be too cumbersome when conventional power sources are employed.

There are many portable macro-scale devices for which conventional power systems are either too cumbersome or add undesirable weight. For example, Bluetooth headsets typically consume about several microwatts (when the data transmission rate is about 500 kbits/s, the power consumption is about 10 nW/bit). In some applications it is desirable to drive such devices by scavenging energy from the sources in the environment such as gentle airflow, vibration, sonic wave, solar, chemical, or thermal energy.

Neuroprosthetics have been developed to restore motor, sensory, and cognitive functions in patients having nerve injuries or diseases by functional electrical stimulation (FES). A broad range of neuroprostheses have been developed and even commercialized to target specific needs, including pain relief, visual/auditory recovery, bladder management, and treatment for neurological disorders such as Alzheimer's disease and Parkinson's disease. Essentially, FES utilizes short bursts of electrical impulses to muscle or neural tissue. The necessary electric energy may be supplied by such technologies as on-board batteries or external energy inputs in forms of external AC power, electromagnetic generators, laser irradiation, etc. However, none of the developed neuroprostheses currently harness energy sources that are readily available within in a biosystem. Harvesting ambient energy in biosystems, especially biomechanical energy that abundantly exists in a human body, could allow self-powered neuroprostheses to operate independently and sustainably.

Therefore, there is a need for a nanogenerator that is configured to harvest ambient energy for local powering of electronic devices.

SUMMARY OF THE INVENTION

The disadvantages of the prior art are overcome by the present invention which, in one aspect, is a generator that includes a substrate, a first electrode layer, a piezoelectric structure, an insulating layer and a second electrode layer. The substrate has a top surface and the first electrode layer is disposed on the top surface of the substrate. The piezoelectric structure extends from the first electrode layer. The piezoelectric structure has a top end. The insulating layer is disposed on the top end of the piezoelectric structure. The second electrode layer is disposed on the non-conductive layer and is spaced apart from the piezoelectric structure.

In another aspect, the invention is a method of making a generator, in which a first electrode layer is applied to a top surface of a substrate. A seed layer is deposited onto the first electrode layer. A dense plurality of vertically-aligned piezoelectric elongated nanostructures is grown from the seed layer. Each nanostructure has a top end. An insulating layer is deposited onto the top ends of the nanostructures. A second electrode layer is deposited onto the insulating layer so that the nanostructures are electrically isolated from the second electrode layer.

In yet another aspect, the invention is a method of making a piezoelectric nanogenerator, in which a first electrode layer is applied to a surface of substrate. A nanostructure seed layer is applied to the first electrode layer. A mask is applied to the nanostructure seed layer. The mask defines a plurality of spaced-apart openings therethrough that expose selected areas of the nanostructure seed layer. A plurality nanostructures is grown from the nanostructure seed layer through the openings. The mask is removed. An insulator layer is applied to the nanostructures. A second electrode layer is deposited onto the insulator layer so that the second electrode layer is electrically isolated from the nanostructures and so that when the nanostructures are deformed by a force, the nanostructures piezoelectricly induce an electrical field that influences the second electrode layer.

These and other aspects of the invention will become apparent from the following description of the preferred embodiments taken in conjunction with the following drawings. As would be obvious to one skilled in the art, many variations and modifications of the invention may be effected without departing from the spirit and scope of the novel concepts of the disclosure.

BRIEF DESCRIPTION OF THE FIGURES OF THE DRAWINGS

FIGS. 1A-1F are a series of schematic drawings showing a first method of making a nanogenerator.

DETAILED DESCRIPTION OF THE INVENTION

Figure 2A:
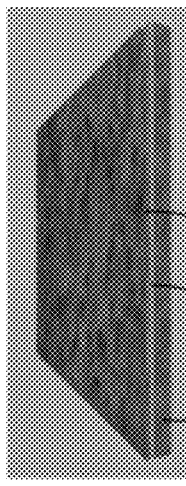
FIGS. 2A-2I are a series of schematic drawings showing a second method of making a nanogenerator.
Figure 2B:
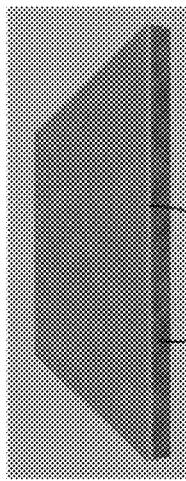
Figure 2C:
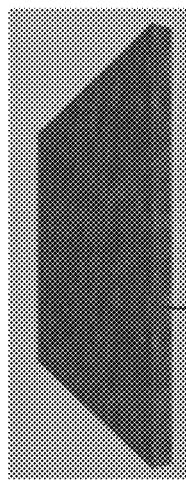
Figure 2D:
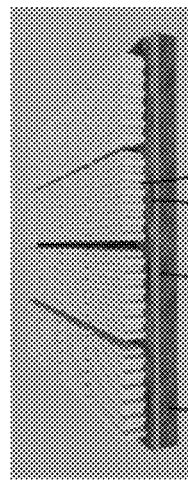
Figure 2E:
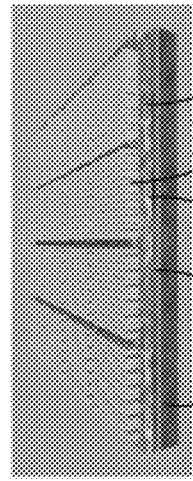

A preferred embodiment of the invention is now described in detail. Referring to the drawings, like numbers indicate like parts throughout the views. Unless otherwise specifically indicated in the disclosure that follows, the drawings are not necessarily drawn to scale. As used in the description herein and throughout the claims, the following terms take the meanings explicitly associated herein, unless the context clearly dictates otherwise: the meaning of "a," "an," and "the" includes plural reference, the meaning of "in" includes "in" and "on."

The following patents, issued to Wang et al., disclose methods of making piezoelectric nanostructures and are incorporated herein by reference for the purpose of disclosing piezoelectric nanostructure growth methods: U.S. Pat. No. 7,351,607, issued on Apr. 1, 2008; U.S. Pat. No. 7,982,370, issued on Jul. 19, 2011; and U.S. Pat. No. 7,898,156, issued on Mar. 1, 2011. The following patent application, filed by Wang et al., discloses methods of making piezoelectric nanostructures and is incorporated herein by reference for the purpose of disclosing piezoelectric nanostructure growth methods: Ser. No. 13/091,855, filed on Apr. 21, 2011.

As shown in FIGS. 1A-1F, in one method of making a nanogenerator 100 a conductive adhesion layer 112 is deposited onto a substrate 110. The substrate 110 could be a rigid substrate, such as a silicon crystal, or it could be a flexible substrate, such as a polystyrene layer. The conductive adhesion layer 112, which acts as a first electrode layer, could include a material such indium tin oxide (ITO) or a metal such as chromium. A nanostructure seed layer 114 is sputtered, or otherwise deposited, onto the conductive adhesion layer 112. A piezoelectric structure, which can include a piezoelectric film or a plurality of elongated piezoelectric nanostructures 116, such as zinc oxide nanowires, is grown from the seed layer 114. (While FIGS. 1B-1F show the nanostructures 116 being spaced apart, in one embodiment they would be densely packed.) An insulating layer 118 is deposited on the top surfaces of the nanostructures 116 and a second electrode layer 120, such as a metal layer (e.g., chromium, silver, aluminum, etc.), is deposited on top of the insulating layer 118. The insulating layer 118 electrically isolates the nanostructures 116 from the second electrode layer 120 so that, as shown in FIGS. 1E and 1F, when a force is applied to the nanogenerator 100 (such as in the direction of the bold arrows), the piezoelectric effect in the nanostructures 116 induces an electric field (represented by the lighter arrows) that influences the second electrode layer 120. In one embodiment, the insulating layer 118 includes a p-type polymer, which was found to show excellent performance. If the nanogenerator 100 is coupled to an energy storage circuit 124 and a load 122, then electrons will flow through the circuit 124 and power the load 122.

The nanogenerator 100 employs the piezoelectric potential generated in the nanowires 116 as it is being dynamically strained under an extremely small force. A transient flow of electrons in an external load as driven by the piezopotential to balance the Fermi levels at the two contacts is the fundamental mechanism of the nanogenerator 100. The power generated by a nanogenerator 100 may not be sufficient to continuously drive a device, but an accumulation of charges generated over a period of time is sufficient to drive the device to work for a few seconds. This is very suitable for applications in the fields of sensing, infrastructure monitoring and sensor networks. A common characteristic for these applications is that there are so many sensors in the system, and each sensor is expected to work independently and wirelessly, but all of them may be linked through a network/internet. Each sensor is not required to work continuously and simultaneously, instead, it will have a "blinking" working mode with a standby status and active status. The standby mode is normally longer, while the active mode is shorter. The energy scavenged and stored during the standby status can be used to drive it in the active mode. This means that these sensors periodically sample from their working environment and transmit data within a fraction of second. The nanogenerator 100 can be used to harvest energy from the environment and store most of the energy when the sensor is in the standby mode. Then the collected energy will be used to trigger the sensor, process and transmit the data in the active mode.

In one experimental embodiment, the power source in this includes the energy harvesting and storage modules. The harvester scavenges some kind of energy (solar, thermal, mechanical and/or chemical) from the environment and stores it in the energy storage module. Thus the collected power is used to drive the other parts of the system. The sensors detect the changes in the environment, while the data processor & controller analyze the information. Then, the signal is sent out by the data transmitter, and simultaneously the response is received. This embodiment is made of a nanogenerator for harvesting mechanical energy, a low-loss full-wave bridge rectifier, a capacitor for storing the energy, an infrared photodetector and a wireless data transmitter.

The nanogenerator used in the integrated system employed a free-standing cantilever beam made of a five-layer structure using densely packed zinc oxide (ZnO) nanowire textured films. The nanogenerator was fabricated on a flexible polyester (PS) substrate (Dura-Lar™, 220 μm in thickness). First, a 5 nm thick Cr adhesion layer followed by a 50 nm thick ZnO seed layer were deposited at the selected rectangular region of 1 cm×1 cm on the top and bottom surfaces of the substrate. The ZnO seed layer is for growing densely packed ZnO nanowires via a wet chemical method. The nutrient solution used in the chemical growth process of ZnO densely packed nanowires textured films was an equal molar aqueous solution of $Zn(NO_3)_2 \cdot 6H_2O$ and hexamethylenetetramine (HMTA), and the concentration was 0.1 M. The nanowire films at the top and bottom surfaces were grown sequentially by placing the substrate at the top of the nutrient solution with one face down. Because of the surface tension, the substrate floated on the solution surface. Growth of ZnO nanowires was carried out in a mechanical convection oven (model Yamato DKN400, Santa Clara, Calif.) at 95° C. for 5 hours. The dimensions of the nanowires were about 150 nm in diameter and 2 μm in length. The ZnO nanowires were grown vertically from the substrate, with a high packing density, and the bottoms of these nanowires were bonded through the ZnO seed layer. Tweezers were used to scratch the top surfaces of these nanowires to establish that the top surfaces of these nanowires were also bonded together tightly in a uniform film. Therefore, the entire ZnO structure could be regarded as a textured film that included fully packed ZnO nanowire arrays between two parallel ZnO films. According to the growth mechanism, the c-axes for these nanowires were their growth direction. Then, a thin layer of poly(methyl methacrylate) (PMMA) (MicroChem 950 k A11) was spin coated on both surfaces of the substrate at the speed of 3000 rpm, followed by a Cr/Au layer deposition on the central rectangular area serving as the electrode of the nanogenerator. Finally, the whole device was fully packaged with polydimethylsiloxane (PDMS) to enhance the mechanical robustness and flexibility. The size of the effective working area of the nanogenerator was 1 cm×1 cm. Two leads were connected to the top and bottom electrodes, respectively. It must be pointed out that the processing temperature was below 100° C. so that the entire process is adaptable for flexible electronics.

There are two scenarios if the ZnO film is made of densely packed nanowires. When the nanogenerator is bent, considering the neutral plane of strain is at the central of the substrate, the nanowire film on the stretched surface of the substrate is subject to a tensile stress, while the one on the compressed surface is under compressive stress. First, if the bonding between the nanowires is very strong to form a solid film with considering that the growth direction of the nanowires is along c-axis (polar direction for ZnO), a tensile stress perpendicular to the nanowires results in a compressive strain along the c-axis direction, thus, creating a piezopotential drop from the roots of the nanowires to their top-ends. At the same time, a corresponding compressive stress is applied to the nanowires on the bottom surface of the substrate, resulting in a tensile strain along the c-axis, thus, the top-ends of the nanowires have a higher piezopotential than their roots. Therefore, the piezopotential drops in the top and bottom ZnO films have the same polarity, and they add up constructively. This piezopotential distribution will introduce induced charges in the top and bottom electrodes, and consequently generating the output voltage.

Secondly, in a case that the bonding between the nanowires is very weak with the possibility of inter-wire sliding/gaps, no piezoelectric potential would be produced by the film on the top surface of the substrate that is under tensile stress. But, considering the nanowires are fully packed and can be squeezed between each other, a piezopotential drop is still created with some degradation by the film at the substrate bottom surface that is subject to a compressive stress. Therefore, a potential drop is also expected between the top and bottom electrodes, but with its magnitude drops less than half in comparison to that in the first case. Also, it is known that the as-grown ZnO nanowires have n-type doping, which can significantly screen the higher piezopotenital side, but leave the lower piezopotential side almost unchanged. Thus, the output voltage of the nanogenerator may be smaller than the theoretically calculated value due to the reasons list above.

For an experimental nanogenerator structure, there are three factors that are important to the power output performance: the length of the nanowires, the thickness of the substrate and the magnitude of the nanogenerator distortion. From the practical point of view, there are two modes to trigger the nanogenerator depending on the form of the mechanical energy scavenged by the nanogenerator s in the environment. For cases where the nanogenerator s are triggered at a constant stress, such as air flow, the calculated results show that the piezopotential between the two electrodes increases as the length of the nanowires is increased or the thickness of the substrate is decreased. When the applied strain is fixed, such as when the nanogenerator is driven by the vibrations of a bridge where the trigger source is rigid, the piezopotential changes in the opposite sense compared to the former case. Thus, by adjusting the two competing factors, the thickness of the substrate and the length of the nanowire arrays, the device can be optimized to maximize its power harvesting efficiency to specific working situations according to the character of the scavenged energy in the environment. Increasing strain can also significantly enhance the output voltage. In addition, ZnO is a biocompatible and environmentally friendly material. The nanowire films can be grown at very low temperature (<100° C.) on any kind of substrate and any shape of substrate.

Utilizing densely grown ZnO nanowire textured films grown on a polymer substrate by low temperature chemical method has been demonstrated as an effective approach for harvesting low-frequency mechanical energy. A nanogenerator with a free cantilever beam construction was fabricated that was made of a five-layer structure: a flexible polymer substrate, ZnO nanowire textured films on its top and bottom surfaces, and electrodes on the surfaces. When it was strained to 0.12% at a strain rate of 3.56% $S^{-1}$, the measured output voltage reached 10 V, and the output current exceeded 0.6 μA for a NG that was 1 $cm^2$ in size (corresponding power density 10 mW/$cm^3$). By storing the energy generated by the nanogenerator, we have demonstrated a self-powered system that can work independently and wirelessly. The system included a nanogenerator, rectification circuit, and capacitor for energy storage, sensor, and RF data transmitter. Wireless signals sent out by the system were detected by a commercial radio at a distance of 5-10 meters. Thus, ZnO nanowire generators are useful for building self-powered systems with capability of long distance data transmission, and have potential applications in wireless biosensing, environmental infrastructure monitoring, sensor networks, personal electronics and even national security.

Figure 2F:
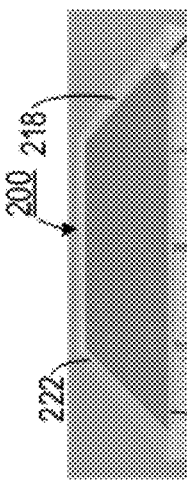
Figure 2G:
Figure 2H:
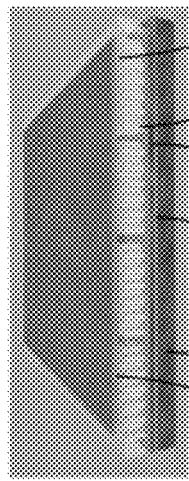
Figure 2I:
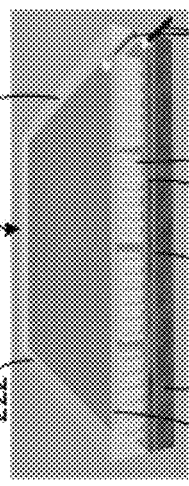
Figure 3:
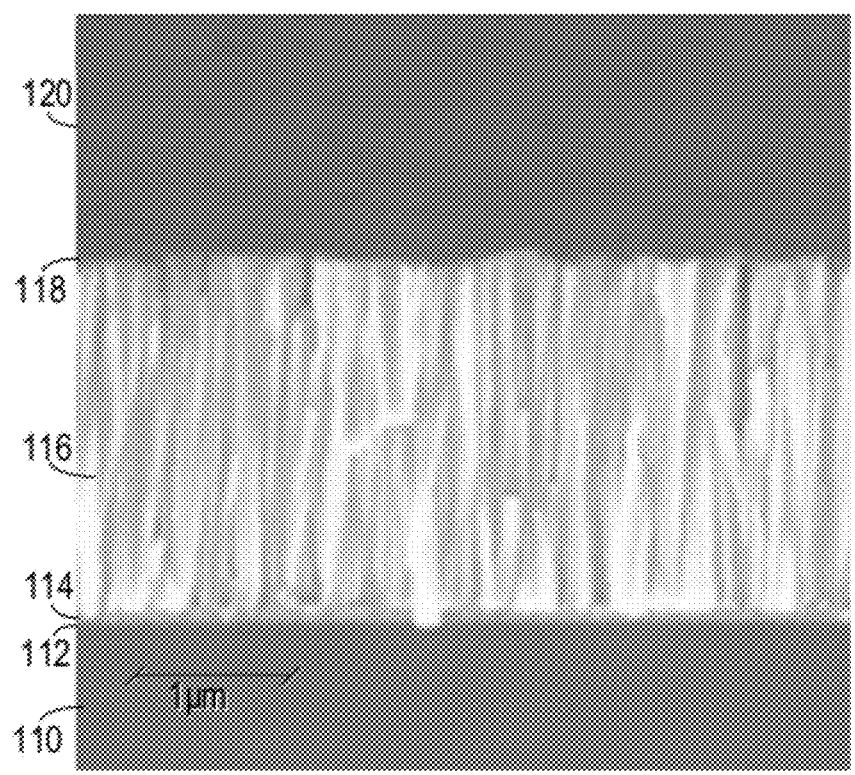
FIG. 3 is a micrograph of a nanogenerator made according to the method shown in FIGS. 1A-1F.

As shown in FIGS. 2A-2I, one embodiment of a nanogenerator 200 allows for substantial power generation while limiting lateral charge transport between different nanostructures 216. This embodiment employs an array of separated blocks of nanostructures 216. This embodiment is constructed by cleaning the top surface of a substrate 210 and then applying an ITO adhesion layer 212 to the clean surface of the substrate 210. The ITO adhesion layer 212 acts as a first electrode layer. A zinc oxide seed layer 214 is applied to the adhesion layer 212 using an RF sputtering process. A mask 230, such as a photolithography mask, is applied to the seed layer 214. The mask 230 defines a plurality of openings 232 therethrough that expose selected areas of the seed layer 214. A plurality of densely packed zinc oxide nanowires 216 is grown from the exposed areas of the seed layer 214. The nanowires 216 are disposed in separated blocks. The spaces between the blocks of nanowires prevent lateral charge transport between the blocks of nanowires 216 thereby reducing inefficiency. The mask 230 may be removed, as shown in FIG. 2F and the nanowires 216 are covered with an insulating layer 218, such as a poly(methyl methacrylate) (PMMA) layer, as shown in FIG. 2G. A second electrode layer 220, which could be a metal layer, is applied to the insulating layer 218 and another PMMA layer 222 is applied to envelope the entire system as a packaging layer. A pair of wires 230 are used to couple the first electrode layer 212 and the second electrode layer 220 to the loads that the nanogenerator 200 powers.

In one experimental embodiment, a pre-cleaned silicon substrate was consecutively deposited with an ITO layer and a ZnO seed layer by RF sputtering. Not only does the ITO layer play a role as a conductive electrode, but also it promotes adhesion between the ZnO seed and the substrate. Photolithography was then performed to open an array of square windows on photoresist with narrow spacing in between. The photoresist serves as a mask so that ZnO nanowires only grow on the exposed seed surface in the subsequent synthesis step by wet mechanical method. Following stripping off any residual photoresist, the nanowires were thermally annealed. Then a layer of PMMA was applied cover the synthesized nanowires by spin-coating, followed by depositing a top metal electrode of aluminum. Finally, another layer of PMMA was used for packaging. Two terminal leads rested on the ITO layer and the aluminum layer for electrical measurement. The process flow is compatible with batch fabrication techniques, which allow multiple silicon wafers to be parallel processed, followed by being diced into individual devices.

The superior performance and robustness of the newly designed nanogenerator may be attributable to the PMMA layer between the nanowires and the metal electrode. Such a thin layer offers a number of advantages. First of all, it is an insulating layer that provides a potential barrier of infinite height, preventing the induced electrons in the electrodes from internal 'leaking' through the ZnO/metal interface. It replaces the Schottky contact in earlier designs. Furthermore, the PMMA fills the gap between nanowires by capillary force and forms a capping at the very top. Consequently when a force is applied along the vertical direction, the stress can be transmitted through the capping layer to all NWs under the force-applied area, greatly enhancing the nanogenerator's efficiency. It also serves as a buffer layer protecting nanowires from intimate interaction with the electrode, improving the nano generator's robustness.

It is also noteworthy that nanowires were selectively grown in photolithography-designated regions. Such segmentation is designed to optimize the nanogenerator's output. Though thermal annealing during the fabrication might help reducing the concentration of free charge carriers, there is still finite conductivity within ZnO nanowires. As a result, free charge carriers within the nanowires will partially screen the piezo-potential, leading to reduced magnitude of it and thus degraded performance of the nanogenerator. The nanowires are so densely packed that they are all electrically connected in parallel. On condition that a force is applied on an area smaller than the device's dimension or the applied force has a non-uniform distribution, only the nanowires located directly beneath the force-applied area will experience strain and thus generate piezopotential, which are referred to as active nanowires. Owing to the presence of segmentation, native free charge carriers within the nanowires that are not directly compressed under the force-applied area (referred to as inactive nanowires) are isolated from the active nanowires. Hence they will not be involved in screening, preserving the piezo-potential from further degradation. However, if no segmentation is made among the nanowires, the free carriers in the inactive nanowires tend to drift toward the high piezopotential side of the active nanowires, which can lower the local piezopotential and the thus the output.

The electric output can be tremendously scaled up by liner superposition. An energy-harvesting pad was fabricated with nine NGs in parallel connection. Being punched by a human palm, the peak value of $V_{oc}$ and $I_{sc}$ exceeded 58 V and 134 µA, respectively. Using such a significant output, the inventors were able to charge a capacitor of 2 µF to over 3 V with less than 20 times of palm impact.

The above described embodiments, while including the preferred embodiment and the best mode of the invention known to the inventor at the time of filing, are given as illustrative examples only. It will be readily appreciated that many deviations may be made from the specific embodiments disclosed in this specification without departing from the spirit and scope of the invention. Accordingly, the scope of the invention is to be determined by the claims below rather than being limited to the specifically described embodiments above.

What is claimed is:

1. A generator, comprising
(a) a substrate having a top surface;
(b) a first electrode layer disposed on the top surface of the substrate;
(c) a piezoelectric structure extending from the first electrode layer, the piezoelectric structure having a top end
(d) a poly(methyl methacrylate) insulating layer disposed on the top end of the piezoelectric structure; and
(e) a second electrode layer disposed on the insulating layer and spaced apart from the piezoelectric structure.

2. The generator of claim 1, wherein the insulating layer comprises a p-type polymer.

3. The generator of claim 1, wherein the piezoelectric structure generates an electric field that influences the second electrode layer when the piezoelectric structure is are deformed and wherein the insulating layer inhibits charge transport from the piezoelectric structure to the second electrode layer.

4. The generator of claim 1, wherein the piezoelectric structure comprises a piezoelectric film.

5. The generator of claim 1, wherein the piezoelectric structure comprises a dense plurality of vertically-aligned piezoelectric elongated nanostructures.

6. The generator of claim 5, wherein the nanostructures comprise densely packed zinc oxide nanowires.

7. The generator of claim 1, wherein the first electrode layer comprises indium tin oxide.

8. The generator of claim 1, wherein the second electrode layer comprises a metal.

9. The generator of claim 1, wherein the substrate comprises a flexible material.

10. The generator of claim 9, wherein the flexible material comprises polystyrene.

11. The generator of claim 1, wherein the substrate comprises silicon.

12. The generator of claim 1, wherein the nanostructures are disposed in a plurality groups, wherein the nanostructures of each group are spaced apart from each adjacent group, thereby reducing lateral charge transfer between the nanostructures.

13. A generator, comprising
(a) a substrate having a top surface;
(b) a first electrode layer disposed on the top surface of the substrate;
(c) a piezoelectric structure extending from the first electrode layer, the piezoelectric structure having a top end
(d) an insulating layer disposed on the top end of the piezoelectric structure; and
(e) a second electrode layer disposed on the insulating layer and spaced apart from the piezoelectric structure and
(f) a packaging layer disposed around the substrate, the first electrode layer, the piezoelectric structure, the insulating layer and the second electrode layer.

14. The generator of claim 13, wherein the insulating layer comprises a p-type polymer.

15. The generator of claim 13, wherein the piezoelectric structure generates an electric field that influences the second electrode layer when the piezoelectric structure is are deformed and wherein the insulating layer inhibits charge transport from the piezoelectric structure to the second electrode layer.

16. The generator of claim 13, wherein the piezoelectric structure comprises a piezoelectric film.

17. The generator of claim 13, wherein the piezoelectric structure comprises a dense plurality of vertically-aligned piezoelectric elongated nanostructures.

18. The generator of claim 13, wherein the first electrode layer comprises indium tin oxide.

19. The generator of claim 13, wherein the second electrode layer comprises a metal.

20. The generator of claim 13, wherein the substrate comprises a flexible material.

21. The generator of claim 13, wherein the substrate comprises silicon.

22. The generator of claim 13, wherein the packaging layer comprises poly(methyl methacrylate).

23. The generator of claim 13, wherein the nanostructures are disposed in a plurality groups, wherein the nanostructures of each group are spaced apart from each adjacent group, thereby reducing lateral charge transfer between the nanostructures.

\* \* \* \* \*